United States Patent
Cifter et al.

(10) Patent No.: US 8,778,391 B2
(45) Date of Patent: Jul. 15, 2014

(54) FLURBIPROFEN AND MUSCLE RELAXANT COMBINATIONS

(75) Inventors: Umit Cifter, Maslak Istanbul (TR); Ali Turkyilmaz, Maslak Istanbul (TR); Hasan Ali Turp, Maslak Istanbul (TR)

(73) Assignee: Sanovel Ilac Sanayi Ve Ticaret Anonim Sirketi, Istanbul (TR)

( * ) Notice: Subject to any disclaimer, the term of this patent is extended or adjusted under 35 U.S.C. 154(b) by 649 days.

(21) Appl. No.: 12/117,378

(22) Filed: May 8, 2008

(65) Prior Publication Data

US 2008/0279933 A1 Nov. 13, 2008

(30) Foreign Application Priority Data

May 8, 2007 (TR) ................ a 2007 03092

(51) Int. Cl.
*A61K 9/20* (2006.01)
*A61K 31/192* (2006.01)
*A61K 31/433* (2006.01)
*A61K 31/704* (2006.01)
*A61K 9/24* (2006.01)

(52) U.S. Cl.
CPC ............ *A61K 31/192* (2013.01); *A61K 31/433* (2013.01); *A61K 31/704* (2013.01); *A61K 9/209* (2013.01)
USPC ....................................................... 424/464

(58) Field of Classification Search
None
See application file for complete search history.

(56) References Cited

U.S. PATENT DOCUMENTS

2003/0185872 A1* 10/2003 Kochinke ............ 424/426

FOREIGN PATENT DOCUMENTS

| EP | 0 837 684 B1 | | 4/1998 | |
|---|---|---|---|---|
| EP | 1 447 450 A1 | | 8/2004 | |
| FR | 2 725 134 | | 4/1996 | |
| GB | 2 197 198 A | | 5/1988 | |
| WO | WO 86/03681 | * | 7/1986 | ............ A61K 45/06 |
| WO | WO 86/03681 A1 | | 7/1986 | |
| WO | WO 98/52545 A1 | | 11/1998 | |
| WO | WO 2005/102338 A1 | | 11/2005 | |

OTHER PUBLICATIONS

Kita et al., Drugs, 2000, 59(3), pp. 487-495.*
Tuzun et al., Joint Bone Spine, 2003, vol. 70, pp. 356-361.*
V. Pietrogrande et al., Studio Policentrico Randomizzato, Doppio Cieco: Muscoril® Capsule E Fiale vs. Placebo in Patologie Ortopedico-Traumatologiche, Ortopedia e Traumatologia Oggi, Oct.-Dec. 1992, pp. 132-137, vol. XII—n. 4; CIC Edizioni Internazionali; Italy.
Sean C. Sweetman, Martindale: The Complete Drug Reference, 35$^{th}$ Edition, 2007, pp. 52-53, vol. I, Published by Pharmaceutical Press, London, UK.
Sean C. Sweetman, Martindale: The Complete Drug Reference, 35$^{th}$ Edition, 2007, p. 1738, vol. I, Published by Pharmaceutical Press, London, UK.
Sean C. Sweetman, Martindale: The Complete Drug Reference, 35$^{th}$ Edition, 2007, p. 1727, vol. I, Published by Pharmaceutical Press, London, UK.

* cited by examiner

*Primary Examiner* — Brian Gulledge
(74) *Attorney, Agent, or Firm* — Kenyon and Kenyon LLP

(57) ABSTRACT

This invention is a novel pharmaceutical composition comprising flurbiprofen or a pharmaceutically acceptable salt thereof in combination with an α-2 adrenergic receptor agonist or a gamma-aminobutiric acid receptor agonist with antiinflammatory, analgesic and myorelaxant activity.

14 Claims, No Drawings

FLURBIPROFEN AND MUSCLE RELAXANT COMBINATIONS

TECHNICAL ASPECT

This invention is a novel pharmaceutical composition comprising flurbiprofen or a pharmaceutically acceptable salt thereof in combination with an α-2 adrenergic receptor agonist or a gamma-aminobutyric acid receptor agonist with anti-inflammatory, analgesic and myorelaxant activity.

More specifically, this invention relates to pharmaceutical composition comprising flurbiprofen or a pharmaceutically acceptable salt thereof in combination with tizanidine or thiocolchicoside with anti-inflammatory, analgesic and myorelaxant activity administrated oral, parenteral, intramuscular and topical in tablet, capsule, injectable preparation, suspension, syrup, sachet, ointment, cream or gel form.

BACKGROUND OF THE INVENTION

Flurbiprofen is a propionic acid derivative and is a known NSAID (non-steroidal anti-inflammatory drug) with analgesic and anti-inflammatory activity. Its chemical structure is shown in the Formula 1.

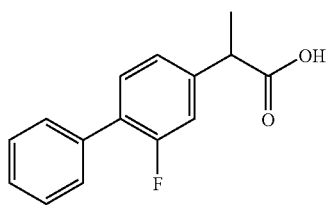

Formula 1

The chemical name of flurbiprofen is 2-Fluoro-α-methyl-[1,1'-biphenyl]-4-acetic acid. It is used in musculoskeletal and joint disorders such as ankylosing spondylitis, osteoarthritis and rheumatoid arthritis, in soft-tissue disorders such as sprains and strains, for postoperative pain and mild to moderate pain including dysmenorrhea and migraine.

Flurbiprofen is also used as lozenges in the symptomatic relief of sore throat. Flurbiprofen sodium is used in eye drops to inhibit intra-operative miosis and to control postoperative inflammation of the anterior segment of the eye. Flurbiprofen axetil has been given in some countries by intravenous injection for severe pain.

For pain and inflammation, flurbiprofen is given in usual doses of 150 mg to 200 mg daily by mouth in divided doses, increased to 300 mg daily in acute or severe conditions if necessary (Sean C Sweetman, Martindale The Complete Drug Reference, thirty-fifth edition 2007, Vol. 1, pages 52 to 53).

Muscle relaxants are used in the management of musculoskeletal and neuromuscular disorders. There are two main types; centrally acting relaxants and directly acting relaxants.

Centrally acting relaxants generally have a selective action on the central nervous system (CNS) and are principally used for relieving painful muscle spasms or spasticity occurring in musculoskeletal and neuromuscular disorders. Their mechanism of action may be due to their CNS-depressant activity.

Tizanidine is an example for this group of muscle relaxants. Its chemical structure is shown in Formula 2.

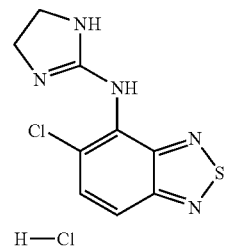

Formula 2

Tizanidine is a $\alpha_2$-adrenergic agonist and acts mainly at spinal and supraspinal levels to inhibit excitatory interneurones. It is used for the symptomatic relief of spasticity associated with multiple sclerosis or with spinal cord injury or disease. It is also used in the symptomatic treatment of painful muscle spasm associated with musculoskeletal conditions (Sean C Sweetman, Martindale The Complete Drug Reference, thirty-fifth edition 2007, Vol. 1, page 1727).

Muscle relaxants also reduce muscle tone and are used in therapy for the treatment of muscle spasm and contractures.

Muscle spasm is one of the main factors responsible for chronic pain; it characterises several pathologies of the locomotor apparatus as well as inflammatory-rheumatic and degenerative orthopaedic pathologies; when it affects joints, they cause not only pain, but also rigidity, which reduces joint mobility and flexibility in the affected part. Muscle contractures also characterize several pathologies of the locomotor apparatus and are one of the main factors responsible for the persistence of the pain associated to these pathologies.

For these reasons the study of molecules endowed with muscle relaxant and antispasmodic properties still raises remarkable interest from the clinical point of view.

As it is known, colchicine is a pseudoalkaloid that has been widely used for a long time in therapy for the treatment of gout. The use of 3-demethyl-thiocolchicine glucoside, known as thiocolchicoside, is also widespread in therapy for treating contractures and inflammatory conditions that affect the muscular system (Ortopedia e traumatologia Oggi XII, n. 4, 1992).

Thiocolchicoside, has been claimed to possess GABA-mimetic and glycinergic actions, in other way we can say that thiocolchicoside is a gamma-aminobutiric acid receptor agonist. Its chemical structure is shown in Formula 3.

Formula 3

It has recently been shown that thiocolchicoside's activity can be ascribed to its ability of interacting with the strychnine-sensitive glycine receptors and therefore that compounds endowed with glycino-mimetic activity can be used in the rheumatologic-orthopedic field for their muscle relaxant properties.

The usual initial dose is 16 mg daily by mouth. It has also been given intramuscularly, in doses up to 8 mg daily, or applied as cream or ointment (Sean C Sweetman, Martindale The Complete Drug Reference, thirty-fifth edition 2007, Vol. 1, page 1738).

Muscle relaxants have been evaluated alone or in combination with conventional analgesics for the treatment of pain. Mixed and unpredictable results have been obtained in a pharmaceutical composition. But flurbiprofen has not previously been combined with an α-2 adrenergic receptor agonist or a gamma-aminobutiric acid receptor agonist in a pharmaceutical composition for the treatment of inflammatory, pain and musculoskeletal diseases.

Tizanidine and/or Thiocolchicoside is a known muscle relaxant agents and sequentially they belong to the groups of α-2 adrenergic receptor agonists and a gamma-aminobutiric acid receptor agonists used in the treatment of painful muscle spasms or spasticity occurring in musculoskeletal and neuromuscular disorders and for treating contractures and inflammatory conditions that affect the muscular system.

PCT application WO 86/03681 A1 (26 Dec. 1984), relates generally to novel pharmaceutical compositions of matter comprising one or more non-steroidal anti-inflammatory drugs other than aspirin, acetaminophen and phenacetin, in combination with at least one skeletal muscle relaxant, and optionally xanthine or a xanthine derivative, such as caffeine, and to methods of using said compositions in the treatment of a variety of skeletal muscle disorders including skeletal muscle spasm, certain orthopedic conditions, disk syndromes, low back pain and the like.

United Kingdom patent application GB 2 197 198 A1 (Sandoz Ltd.) 3 Nov. 1986, describes to novel pharmaceutical preparations comprising ibuprofen and tizanidine with analgesic and myotonolytic activity as well as to methods of inducing analgesia and of treating conditions associated with increased muscle tone. The composition is preferably formulated as a tablet and desirably the weight ratio of tizanidine to ibuprofen is from 1:50 to 1:200, especially 1:100.

French patent FR 2 725 134 B1 (LABORATOIRES LEDERLE) 4 Oct. 1994, relates to a new pharmaceutical composition comprising ibuprofen or a pharmaceutically acceptable salt thereof and thiocolchicoside or a pharmaceutically acceptable salt thereof in a ratio generally ranging between approximately 1:50 and approximately 1:200. According to this invention, the pharmaceutical composition is used in the treatment of the painful muscle syndromes and more particularly in the treatment of the acute lumbagos.

European patent EP 0 837 684 B1 (Sanofi-Synthelabo) 13 Jun. 1995, relates to pharmaceutical compositions containing, in solid form, a diclofenac salt and thiocolchicoside combined with at least one pharmaceutically acceptable carrier are provided for use in therapy.

PCT application WO 98/52545 A1 (THE BOOTS COMPANY PLC) 22 May 1997, relates to pharmaceutical compositions comprising a combination of flurbiprofen with a therapeutically effective amount of one or more active ingredients selected from an antihistamine, a cough suppressant, a decongestant, an expectorant, a muscle relaxant, a centrally acting analgesic, a local anaesthetic, an antibacterial compound, an antiviral compound, an antibiotic compound, an antifungal compound, minerals and vitamins and/or a burn-masking amount of an agent which has a warming effect on the mucosa of the throat.

Also in this application, the treatment comprises the administration to a patient in need thereof of a pharmaceutical composition in the form of a masticable or suckable solid dosage form or a liquid or spray which releases the flurbiprofen and active ingredient(s) and/or burn-masking agent in the oral cavity so as to deliver the active components to the surface of the sore throat.

It is well known that drugs used in the same therapeutic area or even for treating the same indication cannot always be combined a priori with the expectation of at least additive therapeutic effects. The scientific literature is full of examples wherein compounds of different classes, which are used to treat the same indications, cannot be combined into safe and efficacious dosage forms thereby resulting in incompatible drug combinations. The reasons for this unexpected lack of compatibility are varied; however, it is often found that the incompatible drug combinations result in increased side effects, unwanted drug interactions or new side effects. More specifically, in the area of analgesia there are drug combinations that are contraindicated for some or all of these very same reasons.

Conventional analgesic and myorelaxant therapy generally involves administration of a pharmaceutical composition containing one or more different analgesic and muscle relaxant drugs. However, not all combinations of analgesic drugs and muscle relaxant drugs are more suitable, in terms of safety or efficacy, than the administration of a single product.

To date no pharmaceutical compositions or dosage forms comprising a combination of a flurbiprofen and a α-2 adrenergic receptor agonist or a gamma-aminobutiric acid receptor agonist in particular tizanidine or thiocoichicoside, have been made.

DEFINITION OF THE INVENTION

This invention is a pharmaceutical composition comprising flurbiprofen or a pharmaceutically acceptable salt thereof in combination with α-2 adrenergic receptor agonist or a gamma-aminobutiric acid receptor agonist with anti-inflammatory, analgesic and myorelaxant activity administrated oral, parenteral, intramuscular and topical in tablet, capsule, injectable preparation, suspension, syrup, sachet, ointment, cream or gel form.

Novel pharmaceutical composition in the form of a tablet or a capsule administrated orally may provide a significant advance in the available treatments. Such combination therapy may also provide for therapeutic improvements owing to the potential synergistic effect provided by the combination.

Therefore, further aspects of the present invention concern the use of pharmaceutical composition comprising flurbiprofen in combination with α-2 adrenergic receptor agonist or a gamma-aminobutiric acid receptor agonist in particular tizanidine or thiocolchicoside for the manufacture of a medicament for the treatment of painful muscle spasms associated with static and functional disorders of vertebra or occurred in post-operations of osteoarthritis, pain and inflammatory symptoms associated with tissue trauma, degenerative vertebra diseases as torticollis, dorsalgy, lombalgy, disk hernia, neurologic and traumatic disorders associated with spasticity.

The main challenges when combining two or more molecules in the same pharmaceutical form are (a) to guarantee the chemico-physical compatibility between the different active ingredients and/or between the active ingredients and the excipients used; and (b) to insure the therapeutical compatibility between the two active ingredients regarding their pharmacokinetic and/or pharmacological properties in order that the posology of the combined composition allows to obtain safe and efficient plasma levels of both pharmacological agents.

According to main challenges mentioned above, the pharmaceutical composition comprising flurbiprofen in combination with an α-2 adrenergic receptor agonist or a gamma-aminobutiric acid receptor agonist in particular tizanidine or thiocolchicoside have an additive analgesic effect in relief of postoperative pain and provide greater analgesia with the results in a lower incidence of side effects according to priori. These pharmaceutical combinations are administrated oral, parenteral, intramuscular and topical.

The pharmaceutical compositions of the invention include tablets, capsules, injectables, suspensions, syrups, sachets, ointments, creams and gels can be made in accordance with methods that are standard in the art (see, e.g. Remington's Pharmaceutical Sciences, $16^{th}$ edition, A Oslo editor, Easton, Pa. (1980)). Drugs and drug combinations will typically be prepared in admixture with conventional excipients. Suitable carriers include, but are not limited to: water; salt solutions; alcohols; gum arable; vegetable oils; benzyl alcohols; polyethylene glycols; gelatin; carbohydrates such as lactose, amylose or starch; magnesium stearate; talc; silicic acid; paraffin; perfume oil; fatty acid esters; hydroxymethylcellulose; polyvinyl pyrrolidone; etc. The pharmaceutical preparations can be sterilized and, if desired, mixed with auxiliary agents such as: lubricants, preservatives, disintegrants; stabilizers; wetting agents; emulsifiers; salts; buffers; coloring agents; flavoring agents; aromatic substances or sweeteners.

A flurbiprofen and tizanidine or thiocolchicoside composition of the present invention is typically administered in admixture with suitable pharmaceutical diluents, excipients, or carriers, suitably selected with respect to a dosage form for oral administration. Examples of oral dosage forms include tablets (including compressed, coated or uncoated), capsules, hard or soft gelatin capsules, pellets, pills, powders, granules, elixirs, tinctures, colloidal dispersions, dispersions, effervescent compositions, films, sterile solutions or suspensions, syrups and emulsions and the like.

Preferably, the combination of a flurbiprofen with tizanidine or thiocolchicoside will be in the form of a conventional tablet. And it may be granulated by methods such as, dry granulation, low- or high-shear granulation, wet granulation or fluidized-bed granulation. Low-shear granulation, high-shear granulation, wet granulation and fluidized-bed granulation generally produce harder, less friable tablets.

This invention is a pharmaceutical composition, wherein the flurbiprofen or a pharmaceutically acceptable salt with an α-2 adrenergic receptor agonist or a gamma-aminobutyric acid receptor agonist are combined together with at least one pharmaceutically acceptable carrier or excipient.

As mentioned above, this invention comprising in combination of flurbiprofen with tizanidine or thiocolchicoside or pharmaceutically acceptable salt thereof comprising an effective amount of fillers, excipients, binding agents, disintegrants and lubricants or their mixtures. Said invention describes a pharmaceutical combination comprising an effective amount of fillers selected from the group consisting of starch, lactose, microcrystalline cellulose, carboxy cellulose sodium, sucrose; an effective amount of binding agents selected from the group consisting of povidone, hydroxypropyl cellulose, hydroxypropyl methyl cellulose, starch, gelatin; an effective amount of lubricants selected from the group consisting of colloidal anhydrous silica, magnesium stearate, talc, sodium stearyl fumarate; an effective amount of disintegrants selected from the group consisting of microcrystalline cellulose, sodium starch glycollate, croscarmellose sodium, crospovidone, starch and their mixtures An α-2 adrenergic receptor agonist, suitable for use in the context of the present invention is selected from the group comprising tizanidine, clonidine, brimonidine, apraclonidine, guanfacine, guanabenz, mivazerol, dexmedetomidine or a pharmaceutically acceptable salt thereof. Preferably, α-2 adrenergic receptor agonist is a tizanidine or a pharmaceutically acceptable salt thereof.

As mentioned above, this invention comprising active ingredient, flurbiprofen or a pharmaceutically acceptable salt thereof in combination with tizanidine wherein the flurbiprofen is present in an amount of between 100 and 500 mg and the tizanidine is present in an amount of 2 and 36 mg, preferred embodiments an amount of the flurbiprofen is between 100 and 300 mg and the tizanidine is between 6 and 24 mg.

This invention is further defined by reference to the following examples. Although the examples are not intended to limit the scope of the present invention, it should be considered in the light of the description detailed above.

EXAMPLE 1

Flurbiprofen and tizanidine conventional released granules are granulated with high shear granulator or they are obtained from extruder to become pellets by spheronizer and at last they are sieved and dried by fluid bed dryer.

| Content | % amount (w/w) |
| --- | --- |
| Flurbiprofen | 13.0-39.0 |
| Tizanidine HCl | 0.65-1.95 |
| Lactose | 28.0-84.0 |
| Microcristalline cellulose | 5.00-15.0 |
| Croscarmellose sodium | 1.25-3.75 |
| Hydroxypropyl cellulose | 1.50-4.50 |
| Colloidal cilica | 0.10-0.30 |
| Magnesium stearate | 0.50-1.50 |

The granules mentioned above compressed by tablet press machine to obtain conventional tablet forms and these tablets preferably covered by a coating material including conventional coating polymers like Opadry®.

In other preferred embodiments, these granules are filled in a capsule by capsule filling machine to obtain conventional capsule forms in appropriate length.

EXAMPLE 2

Flurbiprofen and tizanidine conventional released granules are granulated with high shear granulator or they are obtained from extruder to become pellets by spheronizer and at last they are sieved and dried by fluid bed dryer.

| Content | % amount (w/w) |
| --- | --- |
| Flurbiprofen | 13.0-39.0 |
| Tizanidine HCl | 1.15-3.45 |
| Lactose | 27.5-82.5 |
| Microcristalline cellulose | 5.00-15.0 |
| Croscarmellose sodium | 1.25-3.75 |
| Hydroxypropyl cellulose | 1.50-4.50 |
| Colloidal cilica | 0.10-0.30 |
| Magnesium stearate | 0.50-1.50 |

The granules mentioned above compressed by tablet press machine to obtain conventional tablet forms and these tablets preferably covered by a coating material including conventional coating polymers like Opadry®.

In other preferred embodiments, these granules are filled in a capsule by capsule filling machine to obtain conventional capsule forms in appropriate length.

Gamma-aminobutyric acid receptor agonists suitable for use in the context of the present invention are selected from the group comprising thiocolchicoside and musimol or a pharmaceutically acceptable salt thereof. Preferably, the gamma-aminobutyric acid receptor agonist is a thiocolchicoside or a pharmaceutically acceptable salt thereof.

As mentioned above, this invention comprising active ingredient, flurbiprofen or a pharmaceutically acceptable salt thereof in combination with thiocolchicoside wherein the flurbiprofen is present in an amount of between 100 and 500 mg and the thiocolchicoside is present in an amount of 2 and 20 mg, preferred embodiments an amount of the flurbiprofen is between 100 and 300 mg and the thiocolchicoside is between 4 and 16 mg.

The invention is further defined by reference to the following example. Although the example is not intended to limit the scope of the present invention, it should be considered in the light of the description detailed above.

EXAMPLE 3

Flurbiprofen and thiocoichicoside conventional released granules are granulated with high shear granulator or they are obtained from extruder to become pellets by spheronizer and at last they are sieved and dried by fluid bed dryer.

| Content | % amount (w/w) |
| --- | --- |
| Flurbiprofen | 15.0-45.0 |
| Thiocolchicoside | 0.75-2.25 |
| Lactose | 20.0-60.0 |
| Microcristalline cellulose | 10.0-30.0 |
| Croscarmellose sodium | 1.50-4.50 |
| Hydroxypropyl cellulose | 2.00-6.00 |
| Colloidal cilica | 0.50-1.50 |
| Magnesium stearate | 0.25-0.75 |

The granules mentioned above compressed by tablet press machine to obtain conventional tablet forms and these tablets preferably covered by a coating material including conventional coating polymers like Opadry®.

In other preferred embodiments, these granules are filled in a capsule by capsule filling machine to obtain conventional capsule forms in appropriate length.

In other preferred embodiments of this invention, the solid dosage form is a bilayer tablet having the flurbiprofen in one layer and an α-2 adrenergic receptor agonist or a gamma-aminobutiric acid receptor agonist particular tizanidine or thiocolchicoside in another layer. The amount of flurbiprofen employed in such bilayer tablets preferably ranges from 100 mg to 500 mg, and more preferably is 100 mg to 300 mg. The amount of tizanidine employed in such bilayer tablets preferably ranges from 2 mg to 36 mg, and more preferably is 6 mg or 24 mg. The amount of thiocolchicoside employed in such bilayer tablets preferably ranges from 2 mg to 20 mg and more preferably is 4 mg or 16 mg.

This invention is further defined by reference to the following example. Although the example is not intended to limit the scope of the present invention, it should be considered in the light of the description detailed above.

EXAMPLE 4

Flurbiprofen Granules

Flurbiprofen granules are granulated with high shear granulator or they are obtained from extruder to become pellets by spheronizer and at last they are sieved and dried by fluid bed dryer.

| Content | % amount (w/w) |
| --- | --- |
| Flurbiprofen | 17.5-52.5 |
| Lactose | 20.0-60.0 |
| Microcristalline cellulose | 9.00-27.0 |
| Croscarmellose sodium | 1.25-3.75 |
| Hydroxypropyl cellulose | 1.75-5.25 |
| Colloidal cilica | 0.25-0.75 |
| Magnesium stearate | 0.25-0.75 |

Thiocolchicoside Granules

Thiocolchicoside granules are granulated with high shear granulator or they are obtained from extruder to become pellets by spheronizer and at last they are sieved and dried by fluid bed dryer.

| Content | % amount (w/w) |
| --- | --- |
| Thiocolchicosiede | 1.25-3.75 |
| Lactose | 37.5-112.5 |
| Starch | 7.50-22.5 |
| Gelatine | 0.75-2.25 |
| Sucrose | 1.50-4.50 |
| Talc | 1.00-3.00 |
| Magnesium stearate | 0.50-1.50 |

The solid dosage form mentioned above is a bilayer tablet having the flurbiprofen granules in one layer and thiocolchicoside granules in second layer. These granules are compressed by 2 layered tablet press machine to obtain bilayer tablet forms and these bilayer tablets preferably covered by a coating material including conventional coating polymers like Opadry II (HP)®.

The invention claimed is:

1. A pharmaceutical composition comprising flurbiprofen or a pharmaceutically acceptable salt thereof in combination with tizanidine or a pharmaceutically acceptable salt thereof, or thiocolchicoside or a pharmaceutically acceptable salt thereof.

2. The pharmaceutical composition of claim 1, wherein the flurbiprofen or pharmaceutically acceptable salts thereof is present in an amount of between 100 and 500 mg.

3. The pharmaceutical composition of claim 1, wherein the tizanidine or pharmaceutically acceptable salt thereof is present in an amount of between 2 and 36 mg.

4. The pharmaceutical composition of claim 1, wherein the thiocolchicoside or pharmaceutically acceptable salt thereof is present in an amount of between 2 and 20 mg.

5. The pharmaceutical composition according to claim 1, wherein the flurbiprofen or pharmaceutically acceptable salt and tizanidine or a pharmaceutically acceptable salt thereof or thiocolchicoside or a pharmaceutically acceptable salt thereof are combined together with at least one pharmaceutically acceptable carrier or excipient.

6. The pharmaceutical composition according to claim 1, wherein said pharmaceutical composition is administered orally, parenterally, intramuscularly or topically.

7. The pharmaceutical composition according to claim 1, wherein said pharmaceutical composition is in the form of a tablet, capsule, sachet, injectable preparation, suspension, syrup, gel, cream or ointment.

8. The pharmaceutical composition of claim 1, wherein the pharmaceutical composition is a solid dosage form provided in the form of a bilayer tablet.

9. The solid dosage form according to claim 8, wherein the solid dosage form takes the form of a bilayer tablet having flurbiprofen or pharmaceutically acceptable salts thereof in one layer and tizanidine or thiocolchicoside or pharmaceutically acceptable salts thereof in another layer.

10. The solid dosage form according to claim 9, wherein the solid dosage form takes the form of a bilayer tablet having flurbiprofen or pharmaceutically acceptable salts thereof in one layer and tizanidine or pharmaceutically acceptable salts thereof in another layer.

11. The solid dosage form according to claim 9, wherein the solid dosage form takes the form of a bilayer tablet having the flurbiprofen or pharmaceutically acceptable salts thereof in one layer and thiocolchicoside or pharmaceutically acceptable salts thereof in another layer.

12. A method of treating painful muscle spasms associated with static and functional disorders of vertebra or occurred in post-operations of osteoarthritis, composing the step of administering a therapeutically-effective amount of the pharmaceutical composition of claim 1 to the patient in need thereof.

13. The method according to claim 12, wherein said pharmaceutical composition is administered orally, parenterally, intramuscularly or topically.

14. The method according to claim 12, wherein said pharmaceutical composition is in the form of a tablet, capsule, sachet, injectable preparation, suspension, syrup, gel, cream or ointment.

* * * * *